(12) United States Patent
Chaturvedula et al.

(10) Patent No.: US 6,432,944 B1
(45) Date of Patent: Aug. 13, 2002

(54) BENZODIAZEPINONE β-AMYLOID INHIBITORS: ARYLACETAMIDOALANYL DERIVATIVES

(75) Inventors: Prasad V. Chaturvedula; Suresh Yeola, both of Cheshire; Shikha Vig, Durham, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/897,545

(22) Filed: Jul. 2, 2001

Related U.S. Application Data

(60) Provisional application No. 60/216,391, filed on Jul. 6, 2000.

(51) Int. Cl.⁷ .................. A61K 31/55; C07D 243/10; C07D 487/00
(52) U.S. Cl. .................. 514/221; 540/500
(58) Field of Search .................. 540/500; 514/221

(56) References Cited

U.S. PATENT DOCUMENTS 5,891,871 A    4/1999   Xia et al. .................. 514/219

FOREIGN PATENT DOCUMENTS

| EP | 652009 | 10/1995 |
|---|---|---|
| WO | WO 94/13319 | 6/1994 |
| WO | WO 95/09838 | 4/1995 |
| WO | WO 97/28135 | 8/1997 |
| WO | WO 97/34878 | 8/1997 |
| WO | WO 98/22430 | 5/1998 |
| WO | WO 98/22433 | 5/1998 |
| WO | WO 98/22441 | 5/1998 |
| WO | WO 98/22493 | 5/1998 |
| WO | WO 98/22494 | 5/1998 |
| WO | WO 98/28268 | 7/1998 |
| WO | WO 98/38177 | 9/1998 |
| WO | WO 99/32453 | 7/1999 |
| WO | WO 99/66934 | 12/1999 |
| WO | WO 99/67219 | 12/1999 |
| WO | WO 99/67220 | 12/1999 |
| WO | WO 99/67221 | 12/1999 |

*Primary Examiner*—Bruck Kifle
(74) *Attorney, Agent, or Firm*—Richard P. Ryan

(57) ABSTRACT

There is provided a series of arylacetamidoalanyl derivatives of benzodiazepinones of Formula I

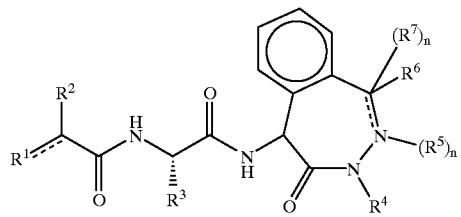

wherein $R^1$ through $R^7$ and n are defined herein, which are inhibitors of β-amyloid peptide (β-AP) production and are useful in the treatment of Alzheimer's Disease and other conditions characterized by aberrant extract cellular deposition of amyloid.

9 Claims, No Drawings

BENZODIAZEPINONE β-AMYLOID INHIBITORS: ARYLACETAMIDOALANYL DERIVATIVES

CROSS REFERENCE TO RELATED APPLICATION

This non-provisional application claims priority from provisional application U.S. Ser. No. 60/216,391 filed Jul. 6, 2000.

FIELD OF THE INVENTION

This invention provides novel benzodiazepinone compounds having drug and bio-affecting properties, their pharmaceutical compositions and method of use. In particular, the invention is concerned with arylacetamidoalanyl derivatives of 2,3-benzodiazepin-4-ones. These compounds uniquely inhibit β-amyloid peptide (β-AP) production, thereby acting to prevent the accumulation of amyloid protein deposits in the brain. More particularly, the present invention relates to the treatment of Alzheimer's Disease (AD).

BACKGROUND OF THE INVENTION

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. There is currently no effective treatment.

There have been many theories relating to the etiology and pathogenesis of AD. These theories were either based on analogies with other diseases and conditions (e.g., slow virus and aluminum theories), or based on pathologic observations (e.g., cholinergic, amyloid, or tangle theories). Genetic analysis can potentially differentiate between competing theories. The identification of mutations in the β-amyloid precursor protein (β-APP) of individuals prone to early onset forms of AD and related disorders strongly supports the amyloidogenic theories.

The β-amyloid precursor protein (β-APP), a large membrane spanning glycoprotein found in tissues of mammals, including humans, is encoded by a gene on the long arm of human chromosome 21. The main constituent of the plaques, tangles and amyloid deposits is known to be β-amyloid peptides (β-AP), composed of approximately 39 to 43 amino acid fragments of β-APP, and in particular, the 40 amino acid fragment known as Aβ1-40. Several lines of evidence support the involvement of β-AP in the pathogenesis of AD lesions. β-AP and related fragments have been shown to be toxic for PC-12 cell lines and primary cultures of neurons, as well as causing neuronal degeneration with accompanying amnesia in rodents. Strong evidence for the role of β-AP in AD consists of observations of genetic β-APP mutations in individuals with certain forms of Familial Alzheimer's Disease (FAD) and the correlation of disease onset with altered release of β-AP fragments.

It is presently believed that the development of amyloid plaques in the brains of AD patients is a result of excess production and/or reduced clearance or removal of β-AP. It is known that a basal level of β-AP production may be a normal process and that multiple pathways for cleavage of β-APP exist. Currently, however, it is unclear which classes of proteinases or inhibitors thereof that would be effective in treating AD. Various peptidergic compounds and their pharmaceutical compositions have been disclosed as useful in inhibiting or preventing amyloid protein deposits in brains of AD and Down's Syndrome patients.

Dovey, et al. in European Patent Application 652,009, published May 10, 1995, disclosed a series of polyamido inhibitors of aspartic proteases, e.g. cathepsin D, for use in inhibiting intracellular β-production.

A series of peptidergic compounds and their administration to patients to prevent abnormal deposition of β-AP was disclosed by Cordell, et al., in WO 95/09838, published Apr. 13, 1995, as a means of treating AD.

Tamburini, et al. in WO 94/13319, published Jun. 23, 1994, disclosed methods for regulating formation of β-AP by use of inhibitors of certain aspartic and serine proteases such as cathepsin D. Specifically, cathepsin D inhibitors were preferred. A series of peptidic compounds resembling pepstatin analogs was disclosed and claimed.

Xia, et al. disclosed substituted 2,3-benzodiazepin-4-ones (1) as being modulators of AMPA receptors for use in treating neurodegenerative disease (U.S. Pat. No. 5,891,871; WO9728135, WO9734878).

(1)

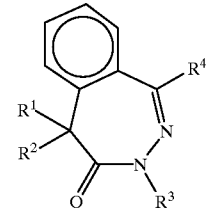

$R^1$ and $R^2$ are, inter alia, hydrocarbon, carbocyclic, aryl and heteroaryl systems but are not alanylamido derivatives.

Audia, et al. have disclosed numerous peptidergic analogs of various azepinone heterocyclics, e.g. (2), but no 2,3-benzodiazepin-4-one derivatives were described. Audia's compounds are reported (2)

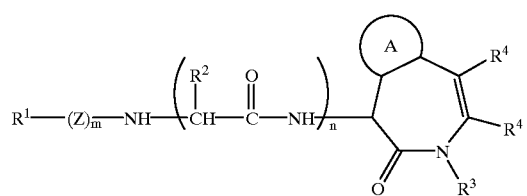

to inhibit β-amyloid formation (WO 9967221, WO 9967220, WO 9967219, WO 9966934, WO 9932453, WO 9838177, WO 9828268, WO 9822494, WO 9822493, WO 9822441, WO 9822433, and WO 9822430).

Nothing in these foregoing references can be construed to describe or suggest the novel alanyl derivatives of 2,3- benzodiazepin-4-ones of this invention or their use to inhibit β-AP production.

SUMMARY DESCRIPTION OF THE INVENTION

A series of arylacetamidoalanyl derivatives of 2,3-benzodiazepin-4-ones have been synthesized. These compounds inhibit the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds to patients suffering from, or susceptible to, these conditions involves reducing β-AP available for accumulation and deposition in brains of these patients.

DETAILED DESCRIPTION OF THE INVENTION

The present invention comprises compounds of Formula I, their pharmaceutical formulations, and their use in inhibiting β-AP production in patients suffering from or susceptible to AD or other disorders resulting from β-AP accumulation in brain tissue. The compounds of Formula I include pharmaceutically acceptable acid and base salts, optical isomers (enantiomers) considered separately or as racemates, and solvates and/or hydrates thereof having the following formula and meanings.

The Formula I compounds are those having the following structure

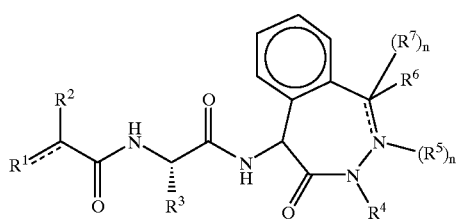

or a pharmaceutically acceptable salt or hydrate thereof wherein $R^1$ is hydrogen, hydroxyl, or oxygen;

$R^2$ is $C_{1-6}$ alkyl, $C_{2-6}$ alkenyl or alkynyl, $C_{3-7}$ cycloalkyl, $C_{5-7}$ cycloalkenyl, aryl, heteroaryl,

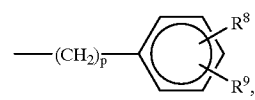

and

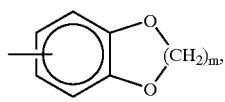

with aryl being phenyl or naphthyl, and heteroaryl being furanyl, thienyl, or pyridinyl;

$R^3$ and $R^4$ are independently selected from $C_{1-6}$ alkyl;

$R^5$ and $R^6$ are independently selected from hydrogen, $C_{1-6}$ alkyl, $C_{2-6}$ alkenyl or alkynyl, $C_{3-7}$ cycloalkyl, $C_{5-7}$ cycloalkenyl,

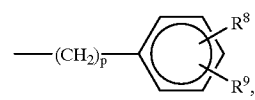

and $-CO_2R^{10}$; or $R^5$ can be taken with $R^4$ or with $R^6$ as a $C_{3-6}$ alkanediyl chain thereby forming a fused ring system;

$R^7$ is hydrogen or can be taken with $R^6$ as =O;

$R^8$ and $R^9$ are independently selected from hydrogen, halogen, trifluoromethyl, $C_{1-6}$ alkyl or alkoxy;

$R^{10}$ is $C_{1-6}$ alkyl;

n is zero or one;

m is one or two;

p is zero, one or two; and the solid and dotted lines are either a single or a double covalent bond with the proviso that when they represent a double bond in the benzodiazepinone ring, n is zero.

There are three subclasses of compounds of Formula I. In subclass A, $R^6$ and $R^7$ are taken together as =O. In subclass B, $R^6$ is selected from the listed moieties that define $R^6$ while $R^7$ is hydrogen. Subclass C has the ring double bond with n being zero.

While the term halogen can mean fluoro, chloro, bromo and iodo, fluoro and chloro are preferred. There are other structurally preferred groups. Phenyl, halo-substituted phenyl, and thienyl are preferred $R^2$ groups.

It is understood that the stereochemistry of the asymmetric carbon being $R^3$ is specified (see compound 1). Another asymmetric carbon is found in the benzodiazepinone ring where the nitrogen atom of the alanyl moiety is attached. There could also be other asymmetric centers, for example in certain of the substituent groups defining $R^2$–$R^6$.

As the compounds of the present invention possess asymmetric carbon atoms, the present invention includes the racemates and diastereomers as well as the individual enantiometric forms of the compounds of Formula I as described herein and in the claims. The use of a single designation such as (R) or (S) is intended to include mostly one stereoisomer. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns.

As indicated, the present invention also pertains to the pharmaceutically acceptable non-toxic salts of the basic centers of these compounds. Such salts include those derived from organic and inorganic acids such as, without limitation, hydrochloric, hydrobromic, phosphoric, sulfuric, methanesulfonic, acetic, tartaric, lactic, succinic, citric, maleic, sorbic, aconitic, salicyclic, phthalic, embonic, and enanthic acids.

The compounds of the present invention may be produced by the processes shown in Reaction Schemes 1, 2 and 3. In Schemes 1, 2 and 3 the symbols $R^1$ to $R^7$ and n are as defined supra. Scheme 1 illustrates a general process showing production of Formula I compounds of subclass A. Scheme 2 shows a general process for synthesis of Formula I compounds of subclass B while Scheme 3 gives a general process for synthesis of subclass C Formula I compounds.

The Scheme 1 process begins with the condensation of hydrazine VII with homophthalic anhydride to give the benzodiazepin-1,4-dione VIA which is converted to the amine IIIA by catalytic hydrogeneration of the azide precursor VA. Reaction of IIIA with an amino-protected alpha-amino acid IV (PG denoted a protecting group such as t-boc) provides the IIA intermediate which is coupled to the carboxylic acid intermediate X to yield the Formula IA product compound.

Scheme 2 illustrates a general synthesis of Formula IB products. Reaction of commercially available 3-isochromanones with suitably substituted hydrazines such as RNH-NHPG (PG denoted a protecting group such as t-boc) to give the alcohol XVII which is converted to cyclic compound VIB under intramolecular Mitsunobu reaction conditions. The amino functionality is introduced through azide VB and subsequent coupling of amine IIIB with an amino-protected amino acid IX provides the intermediate XII. The protecting group PG of XII is removed under acidic conditions to give Formula IIB product or treatment of IIB with an alkylating agent such as R-X to give Formula IB compound.

In Scheme 3 a general synthesis of Formula IC products is shown. Treatment of ortho-formylphenylacetic acid with $R^4$-substituted hydrazine leads to formation of VIC which is converted to the amine intermediate IIIC by catalytic hydrogenation of the azide precursor VC. Reaction of VC with an amine-protected alpha-amino acid IV (PG is a protecting group) leads to the IIC intermediate which is coupled to the carboxylic acid intermediate X to yield the desired Formula IC product.

Greater experimental detail for preparation and reaction of the intermediates displayed in Schemes 1–3 is provided infra. One skilled in synthetic organic chemistry would be adept in modification of the presented synthetic methods in order to make compounds comprising Formula I.

Another aspect of the present invention involves the preparation of the novel compounds of Formula I. In that regard the novel process intermediates of Formula II are useful for the synthesis of products of Formula I.

The present invention also provides a method for the treatment or alleviation of disorders associated with β-amyloid peptide, especially Alzheimer's Disease, which comprises administering together with a conventional adjuvant, carrier or diluent a therapeutically effective amount of a compound of Formula I or a solvate or hydrate thereof.

In the method of the present invention, the term "therapeutically effective mount" means the total amount of each active component of the method that is sufficient to show a meaningful patient benefit, i.e., improve one or more clinical parameters of disease activity, e.g. retention or cognition; or improve disease symptoms such as anxiety or neuromotor control. The subject amount is further characterized by inhibition of β-amyloid peptide production as determined using in vitro assays or in vivo animal models of disease. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means ameliorating one or more clinical indicia of disease activity in a patient having a disease associated with β-amyloid peptide.

Accumulating findings have led to the perception that compounds that demonstrate inhibition of the formation of β-AP from β-APP would be clinically efficacious in treating disorders such as Alzheimer's Disease, Down's Syndrome, and certain forms of brain degeneration. In this regard, the compounds of the instant invention when administered orally or intravenously to experimental animals are capable of entering the CNS and inhibiting production of β-AP formation in experimental animal models of disease.

Representative compounds of the instant series have been tested for their ability to inhibit β-AP formation. Results of this screening assay are shown in Table 1.

Production and detection of Aβ made by cells in culture.

The use of transfected H4 (human neuroglioma) cells stably expressing constructs containing wild-type and variant forms of β-APP have been used to identify inhibitors of Aβ production. Detection of Aβ can be shown by standard techniques such as immunoprecipitation of Aβ from the conditioned medium of $^{35}$S-methionine radiolabeled β-APP-transfected cells such as previously described by Haass, et al., *Nature,* 359, p. 322–325 (1992) and Shoji, et al., *Science,* 258, p. 126–129 (1992) or detection of non-radioactively labeled Aβ by enzyme linked immunosorbent assay (ELISA) as demonstrated by Seubert, et al., *Nature,* 359, p. 325–327 (1992). (The capture antibody is typically a mouse monoclonal (IgG1/kβ-APPa). The antibody recognizes the carboxyl terminal epitope of Aβ. The specificity of the capture antibody insures measurement of Aβ without interference by other secreted β-APP fragments that share amino acid sequence (Aβ1-16) with Aβ but lack the carboxy terminal region. The detecting antibody is typically an affinity purified rabbit polyclonal antibody, specific for the amino terminus of Aβ. In the cell based assay conditioned medium from H4 cells is tested by ELISA for the amount of Aβ present. The cell based assay can been used to identify compounds that inhibit Aβ production. The assay is capable of detecting agents that inhibit cleavage at the β-APP β-secretase and/or the γ-secretase cleavage site as well as detecting any agent that interferes with the production and/or release of Aβ.

A typical ELISA-based assay requires plating of the β-APP transfected cells at a density sufficient for the rapid detection of the secreted Aβ (experimentally predetermined for a particular stable cell population) in a 96-well format. Cells are plated for at least 6 hours prior to the introduction of the test compound at which time the growth medium is replaced by fresh medium containing the agent to be tested. Test agents may typically consist of synthetic compounds, secondary metabolites from bacterial or fungal fermentation extracts, or culture supernatants from mammalian cells. All synthetic agents are initially screened at doses ranging from 10–100 μM or in the case of extracts at sufficient dilution to minimize cytotoxicity. Incubation of the cells with the test agent will continue for approximately 16 hours at which time equal aliquots of media from each sample well is removed and placed into a previously prepared ELISA plate for Aβ quantitation. The ELISA is carried out in a manner described by others (Haass, et al., ibid; Harlow and Lane, Editors, *Antibodies: A Laboratory Manual,* Cold Spring Harbor Press, 1988) and the AD signal quantitated. Results are obtained by analysis of the ELISA plate following development and comparison to the mock treated cell populations and samples in which known amounts of Aβ were added to construct a standard concentration curve. A positive acting compound is one which inhibits cellular production of Aβ relative to levels in control samples by at least 50% at the initial tested concentration and does not show cytotoxicity. If a compound is found to be active then a dose response experiment is performed to determine the lowest dose of compound necessary to elicit the inhibition of the production of Aβ.

TABLE 1

Inhibition of β-Amyloid Peptide by Representative Formula I Compounds
Activity is based on each compound's $IC_{50}$ values:
+ = <3000, + + = <500;
+ + + = <50; + + + + = <10 nM

| Example No. | Activity[a] |
|---|---|
| 24 | 3+ |
| 25 | 3+ |
| 82 | 2+ |
| 20 | 2+ |
| 37 | 3+ |
| 74 | 2+ |
| 73 | 4+ |
| 38 | 2+ |
| 40 | 3+ |
| 41 | 4+ |
| 42 | 3+ |
| 43 | 2+ |
| 44 | 2+ |
| 28 | 2+ |
| 30 | 2+ |
| 31 | 4+ |
| 32 | 3+ |
| 33 | 1+ |
| 34 | 2+ |
| 36 | 2+ |
| 75 | 4+ |
| 76 | 4+ |
| 46 | 2+ |
| 48 | 2+ |
| 49 | 3+ |
| 50 | 2+ |
| 52 | 1+ |
| 54 | 2+ |
| 56 | 1+ |
| 57 | 2+ |
| 60 | 2+ |
| 22 | 3+ |
| 77 | 4+ |
| 89 | 4+ |
| 78 | 4+ |
| 79 | 2+ |
| 80 | 3+ |
| 81 | 2+ |
| 83 | 2+ |
| 84 | 1+ |
| 85 | 4+ |
| 86 | 2+ |
| 23 | 3+ |
| 61 | 4+ |
| 26 | 4+ |
| 64 | 4+ |
| 65 | 3+ |
| 66 | 2+ |
| 63 | 4+ |
| 27 | 4+ |
| 87 | 3+ |
| 88 | 2+ |
| 67 | 4+ |
| 68 | 3+ |
| 69 | 4+ |
| 70 | 3+ |
| 71 | 2+ |
| 72 | 2+ |
| 21 | 3+ |

[a]All compounds of Formula I were found to be less than 3000 nM at $IC_{50}$ concentrations.

Therefore, the compounds of Formula I or pharmaceutical compositions thereof are useful in the treatment of disorders associated with the aberrant extracellular deposition of amyloid, and (as formulated) will be effective to alter one or more clinical indicia of disease activity in a patient in need thereof.

In another embodiment, this invention includes pharmaceutical compositions comprising at least one compound of Formula I in combination with a pharmaceutical adjuvant, carrier or diluent.

In still another embodiment, this invention relates to a method of treatment of disorders characterized by aberrant extracellular deposition of amyloid and which are responsive to the inhibition of β-amyloid peptide in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating systemic (vascular) amyloidosis, pulmonary or muscle amyloidosis, Alzheimer's Disease, Down's Syndrome, or other diseases characterized by extracellular amyloid deposition in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of β-AP inhibition desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to aberrant production and/or extracellular deposition of β-AP as described herein, generally the daily dose will be from about 0.05 mg/kg to about 10 mg/kg and preferably, about 0.1 to 2 mg/kg when administered parenterally. For oral administration, the dose may be in the range from about 1 to about 50 mg/kg and preferably from 0.1 to 2 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus and are uncorrected. Proton magnetic resonance ($^1$H NMR) spectra were recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) or sodium chloride film were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D^{25}$ were determined on a Perkin-Elmer 41 polarimeter in the solvents indicated. Low resolution mass spectra (MS) and the apparent molecular (MH$^+$) or (M-H)$^+$ was determined on a Finnigan TSQ 7000. The element analysis are reported as percent by weight.

Synthesis of Intermediates

A. For IA Products

EXAMPLE 1

1-Methyl-2-(1-methylethyl)hydrazine (VII)

a) To the stirred solution of N-methyl hydrazine (25.00 g, 543.47 mmol ) in THF (600 ml) at −10° C. was added di-tert-butyl dicarbonate (124.5 g, 167 mmol). The resulting mixture was stirred for 1 h and diluted with ethyl acetate (400 ml), further washed with water (1 L), brine (600 ml) and dried over magnesium sulfate. Filtration and concentration in vacuo produced 70 g of crude 1-methylhydrazinecarboxylic acid, 1,1 -dimethylethyl ester.

b) To the solution of above compound (70 g, 479.45 mmol) in ether (1 L) was added acetone (46.34 mL), 3 mL of acetic acid and 500 mg of sodium acetate. The solution was stirred further for an hour and was then concentrated. The resulting residue was diluted with ethyl acetate (800 mL) and washed with water (700 mL), brine (700 mL), dried over magnesium sulfate, filtrated and concentrated to afford 80 g of 2-propanone, methyl-(1,1-dimethylethoxycarbonyl) hydrazone.

c) To lithium aluminium hydride (8.07 g, 212.9 mmol) in anhydrous ether (600 mL) was added the solution of above compound (36 g, 193.54 mmol) in ether (25 mL) (Spialter, et al., *J. Org. Chem.*, 1965, 30, 3278). The suspension was heated to reflux for 1 h, and then after cooling, was quenched with water (20 mL) and the solid was filtered off. The phases were separated and organic phase was washed with brine (400 mL), dried and concentrated. The clear oil was purified by silica gel chromatography (hexane/ethyl acetate, 4:1) to afford 14.1 g (39%) of 1 -methyl-2-(1 -methylethyl) hydrazinecarboxylic acid, 1,1-dimethylethyl ester.

The above compound (14.1 g, 75 mmoL) was dissolved in saturated solution of dioxane (150 mL) with hydrogen chloride gas at 0° C. for 1 h and the solvent was evaporated to afford 1-methyl-2-(1-methylethyl)hydrazine, dihydrochloride (12.3 g, 99%).

EXAMPLE 2

2,3,4,5-Tetrahydro-3-methyl-2-(1-methylethyl)-1H-2,3-benzodiazepin-1,4-dione (VIA)

To the solution of homophthalic anhydride (6.80 g, 41.9 mmol) in 70 mL of glacial acetic acid was added 1-methyl-2-(1-methylethyl)hydrazine, dihydrochloride (6.75 g, 41.9 mmol) in 35 mL of pyridine (Rosen, et al., *J. Heterocyclic Chem.*, 1969, 6, 9–12). The solution was refluxed for 12 h, cooled, diluted with water (300 mL), and extracted with chloroform (3×400 mL). The chloroform extract was washed with 10% hydrochloric acid (600 mL) and 5% sodium bicarbonate (600 mL) , dried over magnesium sulfate and concentrated to dryness. The mixture was purified by silica gel chromatography (hexane/ethyl acetate, 3/1) to afford 2,3,4,5-tetrahydro-3-methyl-2-(1-methylethyl)-1H-2,3-benzodiazepin-1,4-dione (5 g, 51%).

EXAMPLE 3

5-(R,S)-Azido-2,3,4,5-tetrahydro-3-methyl-2-(1-methylethyl)-1H-2,3-benzodiazepin-1,4-dione (VA)

Potassium bis(trimethylsilyl)amide (6.54 g, 32.8 mmol) was added to a −78° C. solution of above compound (3.8 g, 16.3 mmol) in THF (200 mL) followed by the addition of trisyl azide (5.49 g, 17.7 mmol) solution in THF (5 mL) at −78° C. via cannula after 5 minutes (Evans, et al., *J. Amer. Chem. Soc.* 1990, 112, 4011–4030; Butcher, et al., *Tetrahedron Lett.*, 1996, 37 (37), 6685–6688). The reaction mixture was further stirred for another 5 min at −78° C., and 4.5 mL of glacial acetic acid was added and the reaction mixture was warmed to 30° C. over a period of 2 h. Aqueous sodium bicarbonate (200 mL) was added and the mixture was extracted with dichloromethane (3×300 mL). The organic layer was washed with brine (600 mL) dried over magnesium sulfate and concentrated. The resulting solid was purified on silica gel column to afford 5-azido-2,3,4,5-tetrahydro-3-methyl-2-(1-methylethyl)-1 H-2,3-benzodiazepin-1,4-dione (2.72 g, 61%).

EXAMPLE 4

5-Amino-2,3,4,5-tetrahydro-3-methyl-2-(1-methylethyl-1H-2,3-benzodiazepin-1,4-dione (IIIA)

The solution of above azide (2.0 g, 7.32 mmol) in ethyl acetate (50 mL) was treated with hydrogen and 10% palladium on carbon for 1 h. The resulting mixture was filtered through celite pad and the concentration of organic layer afford the amine 5-amino-2,3,4,5-tetrahydro-3-methyl-2-(1-methylethyl)-1H-2,3-benzodiazepin-1,4-dione (1.80, 98%).

EXAMPLE 5

2,3,4,5-Tetrahydro-3-methyl-5(R,S)-[[2S-2-amino-1-oxopropyl]amino]-2-(1-methylethyl) 1 H-2,3-benzodiazepin-1,4-dione (IIA)

a) To the solution of N-boc-(L)-alanine (IV, 1.83 g, 9.7 mmol) in dichloromethane (100 mL) was added N-methyl morpholine (1.29 g, 12.8 mmol) and methyl chloroformate (0.75 mL, 9.72 mmol) at 0° C. The resulting solution was stirred for 10 minutes before the addition of a solution of amine intermediate IIIA (2.0 g, 8.09 mmol) in dichloromethane (5 mL) and it was further stirred for another 1 h. The resulting mixture was washed with 1 N hydrochloric acid (75 mL), sodium bicarbonate (75 mL), brine (75 mL) and dried over magnesium sulfate, filtered and concentrated to afford the crude product. This product was purified further on flash chromatography (hexane/ethyl acetate, 4:1) to afford 2,3,4,5-tetrahydro-3-methyl-5-[[(2S)-2-[(1,1-dimethylethoxycarbonyl)amino]-1-oxopropyl]amino]-2-(1-methylethyl)-1H-2,3-benzodiazepin-1,4-dione(2.6 g, 77%).

b) The above product (2.4 g, 5.7 mmol) was dissolved in dichloromethane (80 mL) and trifluoroacetic acid (4.39 mL, 57.0 mmol). The resulting solution was stirred further for 1 h and then solvent was removed to produce 2,3,4,5-tetrahydro-3-methyl-5-(R,S)-[[(2S)-2-amino]-1-oxopropyl]amino]-2-(1-methylethyl)-1H-2,3-benzodiazepin-1,4-dione, trifluoroacetic acid salt.

c) To the solution of above amine salt (2.0 g, 4.5 mmol) in dichloromethane (100 mL) was added MP-carbonate (3.37 g, 9.25 mmol) and the resulting mixture was stirred for 2 h. Filtration through the celite pad and concentration of the resulting solution afforded the above title amine 2,3,4,5-tetrahydro-3-methyl-5-(R,S)-[[(2S)-2-amino-1-oxopropyl]amino]-2-(1-methylethyl)-1H-2,3-benzodiazepin-1,4-dione (1.35 g, 91%).

EXAMPLE 6

2,3,4,5-Tetrahydro-3-methyl-5(R,S)-[[(2S-2-amino-3-methyl-1-oxobutyl]amino]-2-(1-methylethyl)-1H-2,3-benzodiazepin-1,4-dione (IIA)

a) To a solution of N-boc-(L)-valine (IV, 1.04 g, 4.8 mmol) in dichloromethane (100 mL) was added the N-methyl morpholine (0.56 g, 5.6 mmol) and methyl chloroformate (0.37 mL, 4.8 mmol) at 0° C. The resulting solution was stirred for 10 minutes before the addition of a solution of 5(R,S)-amino-2,3,4,5-tetrahydro-3-methyl-2-(1-methylethyl)-1H-2,3-benzodiazepin-1,4-dione (IIIA, 1.0 g, 4.04 mmol) in dichloromethane (5 mL) and it was further stirred for another 1 h. The resulting mixture was washed with 1N hydrochloric acid (50 mL), sodium bicarbonate (50 mL), brine (50 mL) and dried over MgSO$_4$, filtered and concentrated to afford the crude product. This product was purified further on flash (silica gel) chromatography (hexane/ethyl acetate, 3/2) to afford 2,3,4,5-tetrahydro-3-methyl-5(R,S)-[[(2S)-2-[(1,1-dimethylethoxycarbonyl)amino]-3-methyl-1-oxobutyl]amino]-2-(1-methylethyl)-1H-2,3-benzodiazepin-1,4-dione(1.5 g, 83%).

b) The above compound (1.5 g, 3.36 mmol) was dissolved in dichloromethane (80 mL) and trifluoroacetic acid (5.2 mL, 67.0 mmol). The resulting solution was stirred further for 1 h and then solvent was removed to produce 2,3,4,5-tetrahydro-3-methyl-5(R,S)-[[(2S)-2-amino]-3-methyl-1-oxobutyl]amino]-2-(1-methylethyl)-1H-2,3-benzodiazepin-1,4-dione, trifluoroacetic acid salt.

c) To a solution of above amine salt (0.2 g, 0.43 mmol) in dichloromethane (100 mL) was added MP-carbonate (0.31 g, 0.86 mmol) and the resulting mixture was stirred for 2 h. Filtration through the celite pad and concentration of the resulting solution afforded the above title amine, 2,3,4,5-tetrahydro-3-methyl-5(R,S)-[[(2S)-2-amino-3-methyl-1-oxobutyl]amino]-2-(1-methylethyl)-1H-2,3-benzodiazepin-1,4-dione (0.13 g, 90%).

EXAMPLE 7

2,3,4,5-Tetrahydro-3-methyl-5(R,S)-[[(2S)-2-amino-4-methyl-1-oxopentyl]amino]-2-(1-methylethyl)-1H-2,3-benzodiazepin-1,4-dione (IIA)

a) To the solution of N-boc-(L)-leucine (IV, 1.11 g, 4.8 mmol) in dichloromethane (100 mL) was added the N-methyl morpholine (0.61 mL), 5.6 mmol) and methyl chloroformate (0.37 mL, 4.8 mmol) at 0° C. The resulting solution was stirred for 10 minutes before the addition the solution of 5(R,S)-amino-2,3,4,5-tetrahydro-3-methyl-2-(1-methylethyl)-1H-2,3-benzodiazepin-1,4-dione (1.0 g, 4.04 mmol) in dichloromethane (5 mL) and it was further stirred for another 1 h. The resulting mixture was washed with 1N hydrochloric acid (50 mL), sodium bicarbonate (50 mL), brine (50 mL) and dried over MgSO$_4$, filtered and concentrated to afford the crude product. This product was purified further on flash (silica) chromatography (hexane/ethyl acetate, 6/4) to afford 2,3,4,5-tetrahydro-3-methyl-5(R,S)-[[(2S)-2-[(1-dimethylethoxycarbonyl)amino]-4-methyl-1-oxopentyl]amino]-2-(1-methylethyl)-1H-2,3-benzodiazepin-1,4-dione(2.6 g, 85%).

b) The above compound (1.6 g, 3.4 mmol) was dissolved in dichloromethane (80 mL) and trifluoroacetic acid (5.3 mL, 69.5 mmol). The resulting solution was stirred further for 1 h and then solvent was removed to produce 2,3,4,5-tetrahydro-3-methyl-5(R,S)-[[(2S)-2-amino]-3-methyl-1-oxopentyl]amino]-2-(1-methylethyl)-1H-2,3-benzodiazepin-1,4-dione, trifluoroacetic acid salt.

c) To the solution of above amine salt (0.2 g, 0.42 mmol) in dichloromethane (10 mL) was added MP-carbonate (0.31 g, 0.86 mmol) and the resulting mixture was stirred for 2 h. Filtration through the celite pad and concentration of the resulting solution afforded the above title amine, 2,3,4,5-tetrahydro-3-methyl-5(R,S)-[[(2S)-2-amino-4-methyl-1-oxopentyl]amino]-2-(1-methylethyl)-1H-2,3-benzodiazepin-1,4-dione. (0.41 g, 93%)

B. For IB Products

EXAMPLE 8

2-[2-[2-(Hydroxymethyl)phenyl]-1-oxoethyl]-2-methylhydrazinecarboxylic acid, 1,1-dimethylethyl ester (XVII)

N-(t-Butoxycarbonyl)-N'-methylhydrazine (100 mmol) (Lenman, et al., *J. Chem. Soc. Perkin Trans.*, 1997, 16, 2297–2312; Dutta, et al., *J. Chem. Soc. Perkin Trans.*, 1986, 1655–1664) was added to 3-isochromanone (7.4 g, 50 mmol) (Cheng, et al., *J. Heterocyclic Chem.*, 1995, 32, 73) in a sealed tube followed by 0.2 mL of acetic acid and heated for 12 h at 100° C. The reaction mixture was diluted with EtOAc (100 mL), washed with water (50 mL),1 M HCl (50 mL), brine (50 mL) and dried ($Na_2SO_4$). The desired alcohol 2-[2-[2-(Hydroxymethyl)phenyl]-1-oxoethyl]-2-methylhydrazinecarboxylic acid, 1,1-dimethylethyl ester was purified by flash chromatography (silica) using 50% EtOAc in hexane as eluent. MS (ESI) 295 (M+H).

EXAMPLE 9

2,3,4,5-tetrahydro-3-methyl-4-oxo-1H-2,3-benzodiazepine-2-carboxylic acid, 1,1-dimethylethyl ester (VIB)

The alcohol 2-[2-[2-(Hydroxymethyl)phenyl]-1-oxoethyl]-2-methylhydrazinecarboxylic acid, 1,1-dimethylethyl ester (3.8 g, 12.93 mmol) was dissolved in anhydrous THF (100 mL) added triphenylphosphine (4.1 g, 12.93 mmol) followed by drop wise addition of diisopropyl azodicarboxylate (3.05 mL, 15.5 mmol) and stirring continued for additional 12 h. The reaction mixture was diluted with EtOAc (200 mL), washed with water (50 mL), brine (50 mL) and dried ($Na_2SO_4$). The reaction mixture was purified by flash chromatography (silica) using 40% EtOAc in hexane as eluent to give 2,3,4,5-tetrahydro-3-methyl-4-oxo-1H-2,3-benzodiazepine-2-carboxylic acid, 1,1-dimethylethyl ester in 60% yield.

$^1$H NMR (300 MHz, $CDCl_3$): in δ 7.4-7.1 (m, 4 H), 5.4 (m, 1 H), 4.4 (m, 1 H), 4.16 (d, 1 H), 3.38 (d, 1 H), 3.1 (s, 3 H), 1.46 (s, 9 H).

EXAMPLE 10

5(R,S)-azido-2,3,4,5-tetrahydro-3-methyl-4-oxo-1H-2,3-benzodiazepine-2-carboxylic acid, 1,1-dimethylethyl ester (VB)

To a well stirred solution of 2,3,4,5-tetrahydro-3-methyl-4-oxo-1H-2,3-benzodiazepine-2-carboxylic acid, 1,1-dimethylethyl ester (1.0 g, 3.62 mmol) in anhydrous tetrahydrofuran (30 mL) at −78° C. was added a solution of 0.5 M potassium bis(trimethylsilyl)amide in toluene (9.0 mL, 4.5 mmol). The reaction mixture was stirred for another 15 min followed by addition of a pre-cooled solution (−78° C.) of 2,4,6-triisopropylbenzenesulfonyl azide (trisyl azide) (1.23 g, 4.0 mmol) in THF (0.4M) via a cannula over a period of 1 min (Evans, et al., *J. Amer. Chem. Soc.*, 1990, 112, 4011–4030; Butcher, et al., *Tetrahedron Lett.*, 1996, 37 (37), 6685–6688). After 5 min, acetic acid (1.0 mL, 18 mmol) was added and stirring continued for another 6 h. The reaction mixture was diluted with EtOAc (300 mL), washed with water (300 mL), aqueous $NaHCO_3$ (2×150 mL), 0.5 N HCl (200 mL) and brine (150 mL). The solvent was removed and the 5(R,S)-azido-2,3,4,5-tetrahydro-3-methyl-4-oxo-1H-2,3-benzodiazepine-2-carboxylic acid, 1,1-dimethylethyl ester was purified by flash chromatography (silica) using 10% EtOAc in hexane. The azide was obtained in 60% yield.

$^1$H NMR (300 MHz, $CDCl_3$): in δ 7.4-7.1 (m, 4 H), 5.6 (s, 1 H), 5.42 (m, 1 H), 4.4 (m, 1H), 3.1 (s, 3 H), 1.46 (s, 9 H).

EXAMPLE 11

5(R,S)-amino-2,3,4,5-tetrahydro-3-methyl-4-oxo-1H-2,3-benzodiazepine-2-carboxylic acid,1,1-dimethylethyl ester (IIIB)

To a solution of 5(R,S)-azido-2,3,4,5-tetrahydro-3-methyl-4-oxo-1H-2,3-benzodiazepine-2-carboxylic acid, 1,1-dimethylethyl ester (1.5 g, 7 mmol) in EtOAc (150 mL) was added 10% Pd on carbon (50 mg) and stirred under 1 atmosphere hydrogen. The reaction was closely monitored by TLC using 5% MeOH in $CH_2Cl_2$ as eluent. The reaction was complete after 4 h (TLC) and then filtered the catalyst over a pad of celite. The solvent was removed and the 5(R,S)-amino-2,3,4,5-tetrahydro-3-methyl-4-oxo-1H-2,3-benzodiazepine-2-carboxylic acid, 1,1-dimethylethyl ester was dried under high vacuum. MS (ESI) 292 (M+H).

EXAMPLE 12

N-(3,5-Difluorophenylacetyl)-L-alanine (IX)

To a stirred solution of L-alanine (5.45 g, 70 mmol) in 1 N sodium hydroxide (70 mL, 140 mmol) was added 3,5-difluorophenylacetyl chloride (10.9 g, 57 mmol) dropwise at 0° C. The reaction mixture was stirred overnight at room temperature, washed with ethyl acetate (100 mL). The aqueous phase was acidified with 1 M HCl and then extracted with ethyl acetate (2×200 mL). The organic phase was dried ($Na_2SO_4$) and the desired product was crystallized from hexane/ethyl acetate in 71% yield. MS (ESI) 244 (M+H).

C. IC Products

EXAMPLE 13

4,5-Dihydro-3-methyl-3H-2,3-benzodiazepin-4-one (VIC)

To a solution of ortho-formylphenylacetic acid (10 g, 61 mmol) (Bleasdale, et al., *J. Chem. Soc. Perkin Trans.*, 1991, 1683) in 60 mL of EtOH was added N-methylhydrazine (4.2 g, 91 mmol) and refluxed for 1 h. The reaction mixture cooled, solvent removed and transferred the crude reaction mixture to a vacuum sublimation apparatus. The imine was heated at 140° C. under high vacuum for 1 h and collected the cyclized product by extracting with hot 20% ethyl acetate in hexane (Nagarajan, et al., *J. Med. Chem.*, 1972, 15 (10), 1091). The product was crystallized from 20% ethyl acetate in hexane. 4,5-dihydro-3-methyl-3H-2,3-benzodiazepin-4-one was obtained in 50% yield.

$^1$H NMR (300 MHz, $CDCl_3$): in δ 8.24 (s, 1 H), 7.48-7.25 (m, 4 H), 3.48 (s, 2 H), 3.37 (s, 3 H); MS (ESI+), 175 (M+H).

EXAMPLE 14

5-Azido-4,5-dihydro-3-methyl-3H-2,3-benzodiazepin-4-one (VC)

To a well stirred solution of 4,5-dihydro-3-methyl-3H-2,3-benzodiazepin-4-one (3.0 g, 17.2 mmol) in anhydrous tetrahydrofuran (100 mL) at −78° C. was added a solution of 0.5 M potassium bis(trimethylsilyl)amide in toluene (45 mL, 22.4 mmol). The reaction mixture was stirred for another 15 min followed by addition of a pre-cooled solution of 2,4,6-triisopropylbenzenesulfonyl azide (trisyl azide) (5.8 g, 19 mmol) in THF (0.4M) via a cannula over a period of 2 min (Evans, et al., *J. Amer. Chem. Soc.*, 1990, 112, 4011–4030; Butcher, et al., *Tetrahedron Lett.*, 1996, 37 (37), 6685–6688). After 5 min, acetic acid (4.9 mL, 86 mmol) was added and stirring continued for another 6 h. The reaction mixture was diluted with EtOAc (300 mL), washed with water (300 mL), aqueous $NaHCO_3$ (2×150 mL), 0.5 N HCl (200 mL) and brine (150 mL). The solvent was removed and the 5(R,S)-azido-4,5-dihydro-3-methyl-3H-2,3-benzodiazepin-4-one was purified by flash chromatography (silica) using 10% EtOAc in hexane. The azide was obtained in 75% yield.

¹H NMR (300 MHz, CDCl₃): in δ 8.36 (s, 1H), 7.6 (m, 2 H). 7.44(m, 2 H), 4.84 (s, 1 H), 3.46 (s, 3 H); MS (ESI+), 216 (M+H).

EXAMPLE 15

5-Amino-4,5-dihydro-3-methyl-3H-2,3-benzodiazepin-4-one (IIIC)

To a solution of 5(R,S)-azido-4,5-dihydro-3-methyl-3H-2,3-benzodiazepin-4-one (1.5 g, 7 mmol) in EtOAc (150 mL) was added 10% Pd on carbon (50 mg) and stirred under an atmosphere of hydrogen. The reaction was closely monitored by TLC using EtOAc as eluent. The reaction was complete after 1 h (TLC) and then filtered the catalyst over a pad of celite. The solvent was removed and the 5(R,S)-amino-4,5-dihydro-3-methyl-3H-2,3-benzodiazepin-4-one was dried under high vacuum. This amine product was used immediately in the coupling reactions with various amino acids to yield Formula IIC products.

EXAMPLE 16

5-(R,S)-[[(2S)-2-Amino-1-oxopropyl]amino]-4,5-dihydro-3-methyl-3H-2,3-benzodiazepin-4-one, trifluoroacetic acid salt (IIC)

To a well stirred solution of N(t-butoxycarbonyl)(L)-alanine (IV, 4.73 g, 25 mmol) was added methyl chloroformate (1.93 mL, 25 mmol) at 0° C. followed by Et₃N (3.5, 25 mmol). The reaction mixture stirred for 20 min followed by addition of 5(R,S)-amino-4,5-dihydro-3-methyl-3H-2,3-benzodiazepin-4-one (IIIC) in CH₂Cl₂ (5 mL). Stirring continued for another 2 h, then the reaction mixture diluted with EtOAc (100 mL), followed by washing with water (20 mL), 1M HCl (30 mL), aqueous NaHCO₃ (20 mL), brine (20 mL) and dried (Na₂SO₄). The solvent evaporated and the amine-protected product purified by flash chromatography (50% EtOAc in hexane).

To a stirred solution of the 2,3,4,5-tetrahydro-2,3-dimethyl-5(R,S)-[[(2S)-2-[(1,1-dimethylethoxycarbonyl)amino]-1-oxopropyl]amino]-1H-2,3-benzodiazepin-1,4-dione in CH₂Cl₂ in (20 mL) was added trifluoroacetic acid (20 mL) at room temperature. After 2 h, the solvent removed, added CH₂Cl₂ in (20 mL) and evaporated to remove traces of trifluoroacetic acid. Then, the amine salt was dried under high vacuum for 1 h.

EXAMPLE 17

5(S)-[[(2S)-2-Amino-1-oxopropyl]amino]-4,5-dihydro-3-methyl-3H-2,3-benzodiazepin-4-one, trifluoroacetic acid salt (IIC)

4,5-Dihydro-3-methyl-5(R,S)-[[(2S)-2-[(1,1-dimethylethoxycarbonyl)amino]-1-oxopropyl]amino]-3H-2,3-benzodiazepin-4-one was separated via preparative chiral HPLC using 5% EtOH in hexane as eluent to give both R- and S- isomers of 5-[[(2S)-2-amino-1-oxopropyl]amino]-4,5-dihydro-3-methyl-3H-2,3-benzodiazepin-4-one. The (S)-isomer was converted to 5(S)-[[(2S)-2-amino-1-oxopropyl]amino]-4,5-dihydro-3-methyl-3H-2,3-benzodiazepin-4-one, trifluoroacetic acid salt using the same procedure as described for the diastreomeric mixture.

EXAMPLE 18

5(R)-[[(2S)-2-Amino-1-oxopropyl]amino]-4,5-dihydro-3-methyl-3H-2,3-benzodiazepin-4-one, trifluoroacetic acid salt (IIC)

The (R)-isomer was converted to 5(R)-[[(2S)-2-amino-1-oxopropyl]amino]-4,5-dihydro-3-methyl-3H-2,3-benzodiazepin-4-one, trifluoroacetic acid salt using the same procedure as described for the diastreomeric mixture.

EXAMPLE 19

4,5-Dihydro-3-methyl-5(R,S)-[[(2S)-4-methyl-1-oxopentyl]amino]-3H-2,3-benzodiazepin-4-one, trifluoroacetic acid salt (IIC)

To a well stirred solution of N-(t-butoxycarbonyl)(L)-leucine (IV, 5.8 g, 25mmol) was added methyl chloroformate (1.93 mL, 25 mmol) at 0° C. followed by Et₃N (3.5 mL, 25 mmol). The reaction mixture stirred for 20 min followed by addition of 5(R,S)-amino-4,5-dihydro-3-methyl-3H-2,3-benzodiazepin-4-one (IIIC) in CH₂Cl₂ (5 mL). Stirring continued for another 2 h, then the reaction mixture diluted with EtOAc (100 mL), followed by washing with water (20 mL), 1M HCl (30 mL), aqueous NaHCO₃ (20 mL), brine (20 mL) and dried (Na₂SO₄). The solvent evaporated and the amine-protected product purified by flash chromatography (50% EtOAc in hexane).

To a stirred solution of 4,5-dihydro-3-methyl-5(R,S)-[[(2S)-4-methyl-2-[(1,1-dimethylethoxycarbonyl)amino]-1-oxopentyl]amino]-3H-2,3-benzodiazepin-4-one in CH₂Cl₂ in (20 mL) was added trifluoroacetic acid (20 mL) at room temperature. After 2 h, the solvent removed, added CH₂Cl₂ (20 mL) and evaporated to remove traces of trifluoroacetic acid. Then, the 4,5-dihydro-3-methyl-5-[[(2S)-2-amino-4-methyl-1-oxopentyl]amino]-3H-2,3-benzodiazepin-4-one, trifluoroacetic acid salt was dried under high vacuum for 1 h.

Synthesis of Products
A. Formula IA Compounds

EXAMPLE 20

5-[[(2S)-2-[(3,5-Difluorophenyl)acetylamino]-3-methyl-1-oxobutyl]amino]-2,3,4,5-tetrahydro-3-methyl-2-(1-methylethyl)-1H-2,3-benzodiazepin-1,4-dione To a solution of 2,3,4,5-tetrahydro-3-methyl-5(R,S)-[[(2S)-2-amino-3-methyl-1-oxobutyl]amino]-2-(1-methylethyl)-1H-2,3-benzodiazepin-1,4-dione (IIA, 1.44 mL, 0.28 mmol, 0.2 M solution in dichloromethane) in dichloromethane (2 mL) was added the solution of 3,5-difluorophenyl acetic acid (X, 2.16 mL, 0.43 mmol, 0.2 M solution in dichloromethane) and N-(3-dimethylaminopropyl)-N'-ethyl-carbodiimide polymer (0.72 g, 1.00 mmol) (Desai, et al., *Tet. Lett,* 1993, 34(48), 7685–7688). The resulting mixture was shaken on the shaker for 18 h and the resin was filtered off and washed with dichloromethane (2×1 mL). The combined solvent was collected and evaporated and product was analyzed by HPLC using the column YMC S7 C18 (3.0×50 mm) with a flow rate of 5.0 mL/min and gradient time of 2.0 min., starting with solvent A (10% MeOH—90% H₂O—0.1% TFA), and ending with solvent B (90% MeOH—10% H₂O—0.1% TFA). (70% yield).

¹H NMR (CDCl₃): 0.80–1.25 (m, 12 H), 1.88–2.05 (m, 1 H), 3.25–3.49 (s, 5 H), 4.32–4.52 (m, 2 H), 5.18 (m,1 H), 6.08–6.18 (m,1 H) 5.09–5.10 (d, 1 H), 6.66–7.80 (m, 7 H).

EXAMPLE 21

5-(R,S)-[[(2S)-2-[(3,5-difluorophenyl)acetylamino]-1-oxopropyl]amino]-2,3,4,5-tetrahydro-3-methyl-2-(1-methylethyl)-1H-2,3-benzodiazepin-1,4-dione In a manner similar to example 1, the title compound was prepared by the reaction of 2,3,4,5-tetrahydro-3-methyl-5

(R,S)-[[(2S)-2-amino-1-oxopropyl]amino]-2-(1-methylethyl)-1H-2,3-benzodiazepin-1,4-dione with 3,5-difluorophenylacetic acid. The compound was purified on prep HPLC using the column YMC S5 ODS (20×100 mm) with a flow rate of 40 ml/min and gradient time of 10 min., starting with solvent A (10% MeOH—90% $H_2O$—0.1% TFA), and ending with solvent B (90% MeOH—10% $H_2O$—0.1% TFA). (75% yield). MS (ESI) 473.09 (M+H); $R_f$ 1.31

EXAMPLE 22

2,3,4,5-Tetrahydro-3-methyl-5(R,S)-[[(2S)-4-methyl-1-oxo-2-(phenylacetylamino)pentyl]amino]-2-(1-methylethyl)-1H-2,3-benzodiazepin-1,4-dione In a manner similar to example 1, the title compound was prepared by the reaction of 2,3,4,5-tetrahydro-3-methyl-5 (R,S)-[[(2S)-2-amino-4-methyl-1-oxopentyl]amino]-2-(1-methylethyl)-1H-2,3-benzodiazepin-1,4-dione with phenylacetic acid. The compound was purified on prep HPLC using the column YMC S5 ODS (20×100 mm) with a flow rate of 40 ml/min and gradient time of 10 min., using the solvent composition of solvent A as 10% MeOH—90% $H_2O$—0.1% TFA, and solvent B as 90% MeOH—10% $H_2O$—0.1% TFA. (70% yield). MS (ESI) 479.22 (M+H); $R_f$ 1.42

EXAMPLE 23

2,3,4,5-Tetrahydro-5(R,S)-[[(2S)-2-[(2S)-(hydroxy)(phenyl)acetylamino]-1-oxopropyl]amino]-3-methyl-2-(1-methylethyl)-1H-2,3-benzodiazepin-1 4-dione In a manner similar to example 1, the title compound was prepared by the reaction of 2,3,4,5-tetrahydro-3-methyl-5 (R,S)-[[(2S)-2-amino-1-oxopropyl]amino]-2-(1-methylethyl)-1H-2,3-benzodiazepin-1,4-dione with (S)-mandelic acetic acid. The compound was purified on prep HPLC using the column YMC S5 ODS (20×100 mm) with a flow rate of 40 ml/min and gradient time of 10 min., starting with solvent A (10% MeOH—90% $H_2O$—0.1% TFA), and ending with solvent B (90% MeOH—10% $H_2O$—0.1% TFA). (11% yield). MS (ESI) 453.16 (M+H); $R_f$ 1.05

B. Formula IB Compounds

EXAMPLE 24

5(R,S)-[[(2S)-2-[(3,5-Difluorophenyl)acetylamino-1-oxopropyl]amino]-2,3,4,5-tetrahydro-3-methyl-4-oxo-1H-2,3-benzodiazepine-2-carboxylic acid, 1,1-dimethylethyl ester (XII)

5(R,S)-amino-2,3,4,5-tetrahydro-3-methyl-4-oxo-1H-2,3-benzodiazepine-2-carboxylic acid, 1,1-dimethylethyl ester was dried under high vacuum. The amine (0.64 g, 2.2 mmol) in $CH_2Cl_2$ (5 mL) was then added to a well-stirred solution of N-(3,5-difluorophenylacetyl)-L-alanine (0.59 g, 2.42 mmol), 1-(3-dimethylaminopropyl)-3-ethylcarbodiimide methiodide (0.72 g, 2.42 mmol) 1-hydroxybenzotriazole (0.33 g, 2.42 mmol), triethylamine (0.34 mL, 2.42 mmol) in DMF (20 mL). After 2 h, the reaction mixture diluted with EtOAc (200 mL), washed with water (3×100 mL), 10% citric acid (50 mL), brine (50 mL) and dried ($Na_2SO_4$). Purification by flash chromatography (silica) using 50% EtOAc in hexane gave 5(R,S)-[[(2S)-2-[(3,5-difluorophenyl)acetylamino]-1-oxopropyl]amino]-2,3,4,5-tetrahydro-3-methyl-4-oxo-1H-2,3-benzodiazepine-2-carboxylic acid, 1,1-dimethylethyl ester in 75% yield.

$^1$H NMR (300 MHz, $CDCl_3$): in δ 7.4-6.8 (m, 7 H), 6.1 (m, 1 H), 5.42 (m, 1 H), 4.7 (m, 1 H), 4.4 (m, 1 H), 3.42 (m, 2 H), 3.1 (s, 3 H), 1.43 (s, 9 H), 1.3 (m, 3 H); MS (ESI) 539 (M+Na); $R_f$ =1.73

EXAMPLE 25

5(R,S)-[[(2S)-2-[(3,5-Difluorophenyl)acetylamino]-1-oxopropyl]amino]-2,3,4,5-tetrahydro-3-methyl-1H-2,3-benzodiazepin-4-one (IIB)

To stirred solution of 5(R,S)-[[(2S)-2-[(3,5-difluorophenyl)acetylamino]-1-oxopropyl]amino]-2,3,4,5-tetrahydro-3-methyl-4-oxo-1H-2,3-benzodiazepine-2-carboxylic acid, 1,1-dimethylethyl ester (800 mg, 1.55 mmol) in $CH_2Cl_2$ (20 mL) was added trifluoroacetic acid (40 mL) at room temperature. After 2 h, the solvent was removed. The product was dissolved in $CH_2Cl_2$ (40 mL) and removed the solvent to remove traces of TFA. The compound was obtained in 98% yield and dried under high vacuum for 12 h.

$^1$H NMR (300 MHz, $CDCl_3$): in δ 7.6-6.8 (m, 8 H), 4.75 (m, 1 H), 4.4 (m, 2 H), 3.6 (s, 2 H), 3.2 (s, 3 H), 1.44 (m, 3 H); MS (ESI) 417 (M+H); $R_f$=1.25

C. Formula IC Compounds

EXAMPLE 26

4,5-Dihydro-3-methyl-5(R,S)-[[(2S)-4-methyl-1-oxo-2-[(3-thienyl)acetylamino]pentyl]amino]-3H-2,3-benzodiazepin-4-one To a well stirred solution of 4,5-dihydro-3-methyl-5(R,S)-[[(2S)-2-amino-4-methyl-1-oxopentyl]amino]-3H-2,3-benzodiazepin-4-one, trifluoroacetic acid salt (104 mg, 0.25 mmol) in $CH_2Cl_2$(6 mL) was added 3-thiopheneacetic acid (43 mg, 0.3 mmol), benzotriazole-1-yl-oxy-tris-pyrrolidino-phosphonium hexafluorophosphate (PyBOP) (156 mg, 0.3 mmol) and triethylamine (0.13 mL, 0.9 mmol). The reaction mixture stirred for another 12 h, diluted with EtOAc (10 mL), washed with water (10 mL), 1M HCl (10 mL), aqueous $NaHCO_3$ (10 mL), brine (10 mL) and dried ($Na_2SO_4$). The product is purified by flash chromatography (silica) using 40% EtOAc as eluent in hexane. 4,5-Dihydro-3-methyl-5 (R,S)-[[[(2S)-4-methyl-1-oxo-2-[(3-thienyl)acetylamino] pentyl]amino]-3H-2,3-benzodiazepin-4-one was obtained in 75% yield. The product was analyzed by HPLC using the column YMC S7 C18 (3.0×50 mm) with a flow rate of 5.0 mL/min and gradient time of 2.0 min., starting with a solvent composition of 10% MeOH—90% $H_2O$—0.1% TFA and ending with a solvent composition of 90% MeOH—10% $H_2O$—0.1% TFA.

$^1$H NMR (300 MHz, $CDCl_3$): in δ 8.36 (s, 1H), 7.78-6.9 (m, 7 H), 5.10-5.02 (m, 1 H), 4.7-4.6 (m, 1 H), 3.6 (s, 2 H), 3.4 (s, 3 H), 1.8, 1.4 (m, 3 H), 0.9 (m, 6 H); MS (ESI+), 427 (M+H); $R_f$=1.36

EXAMPLE 27

4,5-Dihydro-3-methyl-5(R,S)-[[(2S)-4-methyl-1-oxo-2-[(2-thienyl)acetylamino]pentyl]amino]-3H-2,3-benzodiazepin-4-one To a stirred solution of 4,5-dihydro-3-methyl-5(R,S)-[[(2S)-2-amino-4-methyl-1-oxopentyl]amino]-3H-2,3-benzodiazepin-4-one, trifluoroacetic acid salt (104 mg, 0.25 mmol) in $CH_2Cl_2$ (5 mL) was added 2-thiopheneacetyl chloride (48 mg, 0.3 mmol) and triethylamine (0.13 mL, 0.9 mmol). After 12 h, the reaction mixture was diluted with EtOAc (15 mL), washed with aqueous $NaHCO_3$ (10 mL), 1 M HCl (5 mL), brine and dried ($Na_2SO_4$). The product is purified by preparative HPLC starting from 30% solvent B (90% MeOH—10% $H_2O$—0.1% TFA)—70% solvent A (10% MeOH—90% $H_2O$—0.1% TFA) to 100% solvent B over a gradient time of 6 min and at a flow rate of 30 mL/min (column YMC S5 ODS 30×100 mm). The product was obtained in 72% yield. The product was analyzed by HPLC using the column YMC S7 C18 (3.0×50 mm) with a flow rate of 5.0 mL/min and gradient time of 2.0 min., starting with a solvent composition of 10% MeOH—90% $H_2O$—0.1% TFA and ending with a solvent composition of 90% MeOH—10% $H_2O$—0.1% TFA. MS (ESI) 449 (M+Na); $R_f$=1.37

In a manner similar to that of Examples 20–23, the following IA products, shown in Table 2, were synthesized.

TABLE 2

Formula IA Products

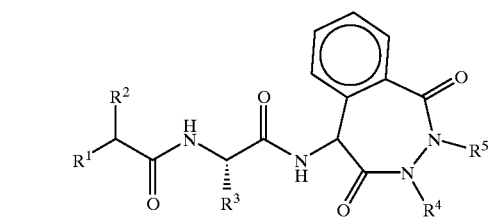

IA

| Ex. No. | $R^1$ | $R^2$ | $R^3$ | $R^4$ | $R^5$ | Yield % |
|---|---|---|---|---|---|---|
| 28 | H | 3,4-diClPhCH$_2$— | CHMe$_2$ | Me | CHMe$_2$ | 75 |
| 29 | H | 3,5-diCF$_3$PhCH$_2$— | CHMe$_2$ | Me | CHMe$_2$ | 92 |
| 30 | H | cy-hex-CH$_2$— | CHMe$_2$ | Me | CHMe$_2$ | 90 |
| 31 | H | 3-thienyl-CH$_2$— | CHMe$_2$ | Me | CHMe$_2$ | 95 |
| 32 | H | 3-F—Ph—CH$_2$— | CHMe$_2$ | Me | CHMe$_2$ | 95 |
| 33 | H | 3-pyridinyl-CH$_2$— | CHMe$_2$ | Me | CHMe$_2$ | 90 |
| 34 | H | 4-MePh—CH$_2$— | CHMe$_2$ | Me | CHMe$_2$ | 95 |
| 35 | H | 3,5-diMeO—CH$_2$— | CHMe$_2$ | Me | CHMe$_2$ | 95 |
| 36 | H | PhCH$_2$ | CHMe$_2$ | Me | CHMe$_2$ | 95 |
| 37 | H | 3,5-diFPhCH$_2$— | CH$_2$CHMe$_2$ | Me | CHMe$_2$ | 70 |
| 38 | H | 3,4-diClPhCH$_2$— | CH$_2$CHMe$_2$ | Me | CHMe$_2$ | 73 |
| 39 | H | 3,5-diCF$_3$PhCH$_2$— | CH$_2$CHMe$_2$ | Me | CHMe$_2$ | 89 |
| 40 | H | cy-hex-CH$_2$— | CH$_2$CHMe$_2$ | Me | CHMe$_2$ | 90 |
| 41 | H | 3-thienyl-CH$_2$— | CH$_2$CHMe$_2$ | Me | CHMe$_2$ | 89 |
| 42 | H | 3-F—PhCH$_2$— | CH$_2$CHMe$_2$ | Me | CHMe$_2$ | 90 |
| 43 | H | 3-pyridinyl-CH$_2$— | CH$_2$CHMe$_2$ | Me | CHMe$_2$ | 90 |
| 44 | H | 4-MePhCH$_2$— | CH$_2$CHMe$_2$ | Me | CHMe$_2$ | 95 |
| 45 | H | 3,5-diMeOPhCH$_2$— | CH$_2$CHMe$_2$ | Me | CHMe$_2$ | 55 |
| 46 | H | 3,4-diClPhCH$_2$— | Me | Me | CHMe$_2$ | 97 |
| 47 | H | 3,5-diCF$_3$PhCH$_2$— | Me | Me | CHMe$_2$ | 40 |
| 48 | H | cy-hex-CH$_2$— | Me | Me | CHMe$_2$ | 70 |
| 49 | H | 3-thienyl-CH$_2$— | Me | Me | CHMe$_2$ | 97 |
| 50 | H | 3-FPhCH$_2$— | Me | Me | CHMe$_2$ | 23 |
| 51 | H | 3-pyridinylCH$_2$— | Me | Me | CHMe$_2$ | 20 |
| 52 | H | 4-MePhCH$_2$— | Me | Me | CHMe$_2$ | 99 |
| 53 | H | 3,5-diMeOPhCH$_2$— | Me | Me | CHMe$_2$ | 66 |
| 54 | H | 3-ClPhCH$_2$— | Me | Me | CHMe$_2$ | 97 |
| 55 | H | 2-pyridinylCH$_2$— | Me | Me | CHMe$_2$ | 18 |
| 56 | H | 1,3-benzodioxol-5-ylCH$_2$— | Me | Me | CHMe$_2$ | 90 |
| 57 | H | 4-FPhCH$_2$— | Me | Me | CHMe$_2$ | 96 |
| 58 | H | 2-naphthyl | Me | Me | CHMe$_2$ | 50 |
| 59 | H | 4-pyridinylCH$_2$— | Me | Me | CHMe$_2$ | 39 |
| 60 | H | PhCH$_2$— | Me | Me | CHMe$_2$ | 75 |
| 61 | H | 3-FPhCH$_2$— | Me | Me | CHMe$_2$ | 4 |

In similar fashion, the procedures of Examples 26–27 can be modified to provide additional examples of Formula IC compounds as set forth in Table 3.

TABLE 3

Formula IC Products

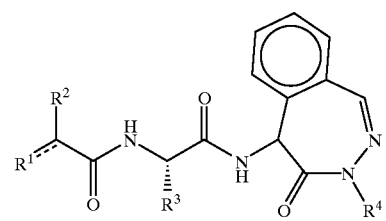

IC

| Ex. No. | $R^1$ | $R^2$ | $R^3$ | $R^4$ | Yield % |
|---|---|---|---|---|---|
| 62 | O | Ph | CH$_2$CHMe$_2$ | Me | 91 |
| 63 | (S)—OH | Ph | CH$_2$CHMe$_2$ | Me | 80 |
| 64 | H | 3,5-diFPhCH$_2$— | CH$_2$CHMe$_2$ | Me | 91 |
| 65 | H | 4-FPhCH$_2$— | CH$_2$CHMe$_2$ | Me | 80 |
| 66 | H | 4-MePhCH$_2$— | CH$_2$CHMe$_2$ | Me | 80 |
| 67 | H | 3-FPhCH$_2$— | CH$_2$CHMe$_2$ | Me | 70 |
| 68 | H | 2-FPhCH$_2$— | CH$_2$CHMe$_2$ | Me | 72 |
| 69 | H | 3-ClPhCH$_2$— | CH$_2$CHMe$_2$ | Me | 75 |
| 70 | H | cy-hex-CH$_2$— | CH$_2$CHMe$_2$ | Me | 60 |
| 71 | H | 2-Cl-4-FPhCH$_2$— | CH$_2$CHMe$_2$ | Me | 70 |
| 72 | (R)—OH | Ph | CH$_2$CHMe$_2$ | Me | 50 |
| 73 | H | 3,5-diFPhCH$_2$— | Me | Me | 90 |
| 74 | H | 3,5-diFPhCH$_2$— | Me | Me | 90 |
| 75 | (S)—OH | 3,5-diFPhCH$_2$— | Me | Me | 90 |
| 76 | (R)—OH | 3,5-diFPhCH$_2$— | Me | Me | 90 |
| 77 | H | 3-thienylCH$_2$— | Me | Me | 90 |
| 78 | H | 3-ClPhCH$_2$— | Me | Me | 65 |
| 79 | H | 4-FPhCH$_2$— | Me | Me | 70 |
| 80 | H | cy-hex-CH$_2$— | Me | Me | 70 |
| 81 | H | 3-pyridinylCH$_2$— | Me | Me | 53 |
| 82 | (R)—OH | Ph | Me | Me | 65 |
| 83 | H | 3,4-diClPhCH$_2$— | Me | Me | 83 |
| 84 | H | 4-FPhCH$_2$— | Me | Me | 82 |
| 85 | H | 3-FPhCH$_2$— | Me | Me | 85 |
| 86 | H | 2-naphthyl | Me | Me | 80 |
| 87 | H | —CHMe$_2$ | CH$_2$CHMe$_2$ | Me | 60 |
| 88 | H | PhCH$_2$CH$_2$— | CH$_2$CHMe$_2$ | Me | 63 |

TABLE 3-continued
Formula IC Products
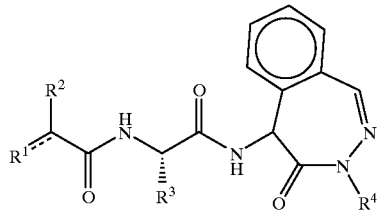
| Ex. No. | $R^1$ | $R^2$ | $R^3$ | $R^4$ | Yield % |
|---|---|---|---|---|---|
| 89 | H | 2-thienyl | Me | Me | ? |
Scheme 1
General Preparation of IA Products
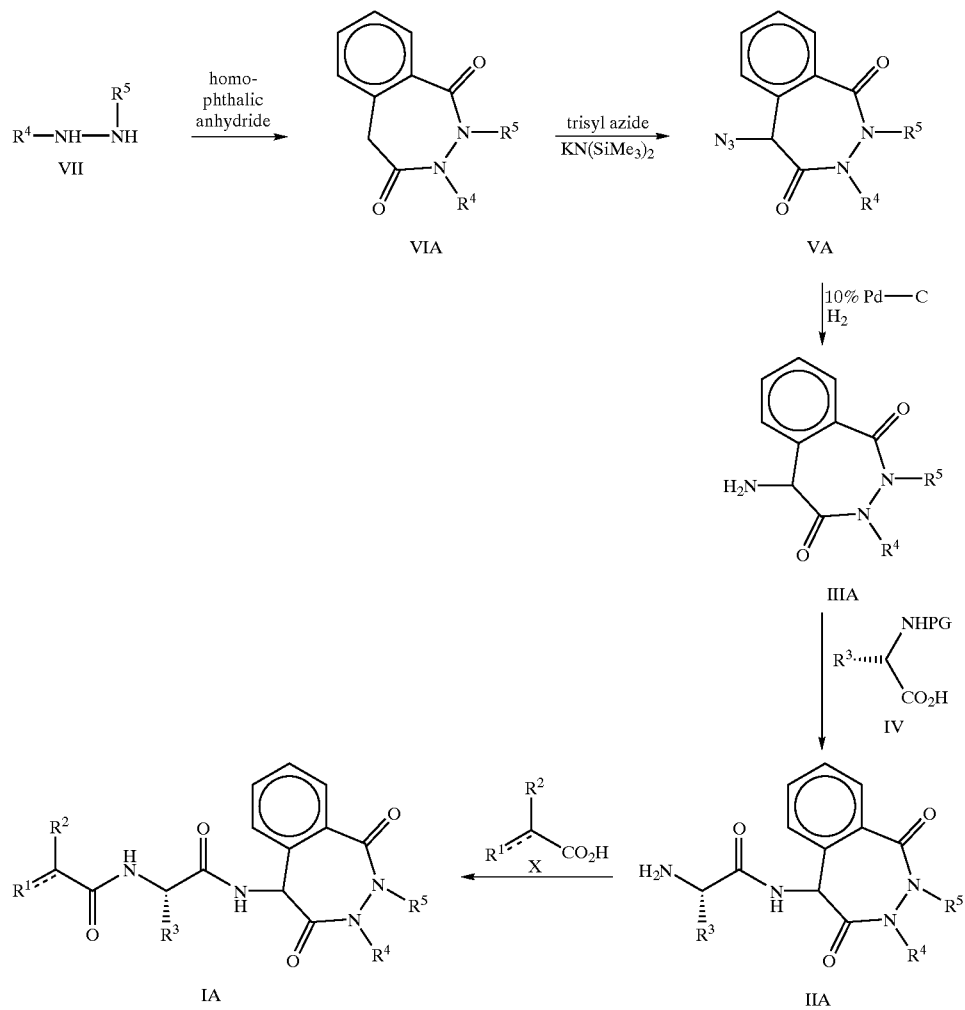

Scheme 2
General Preparation of IB Products
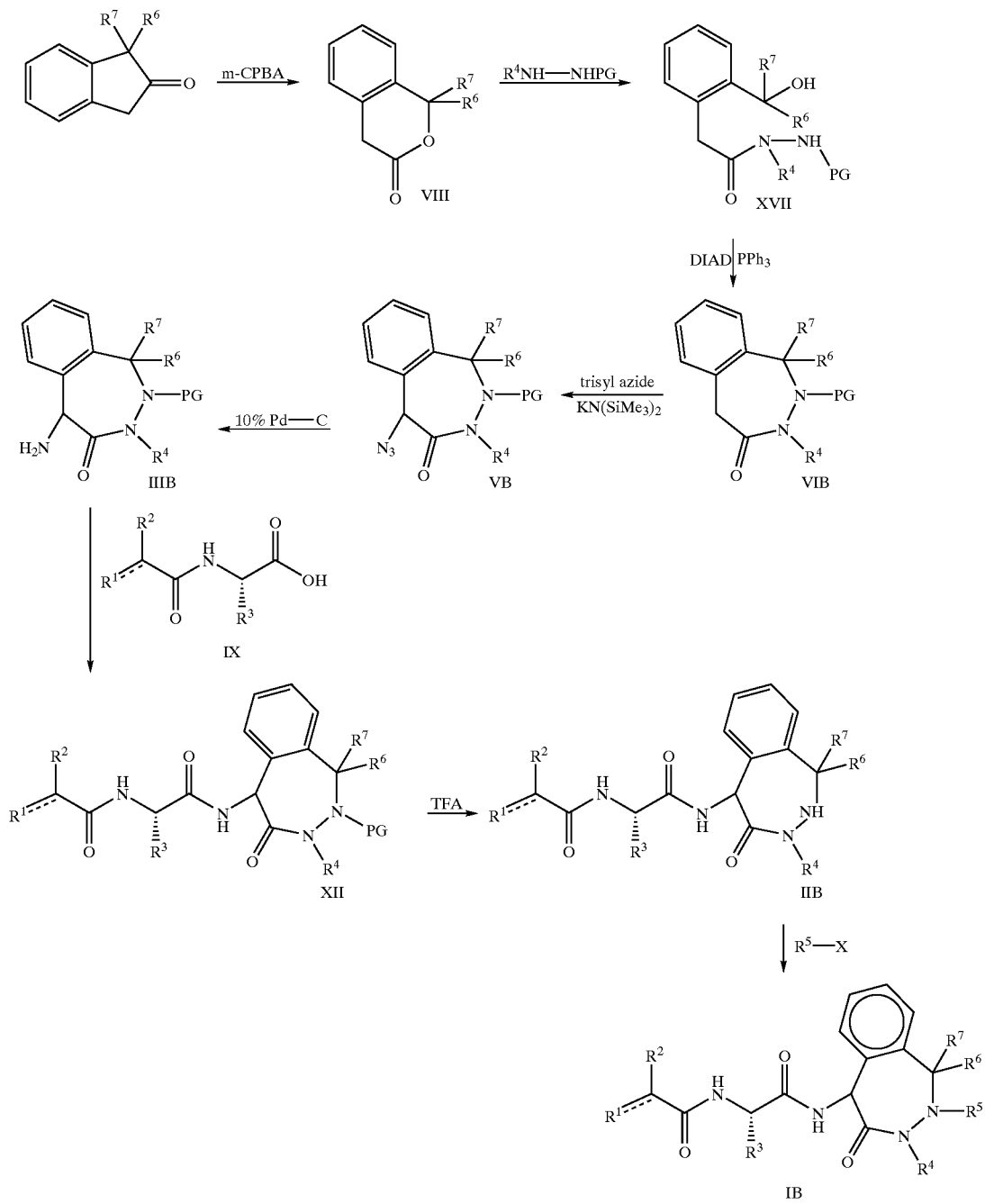

Scheme 3
General Preparation of IC Products

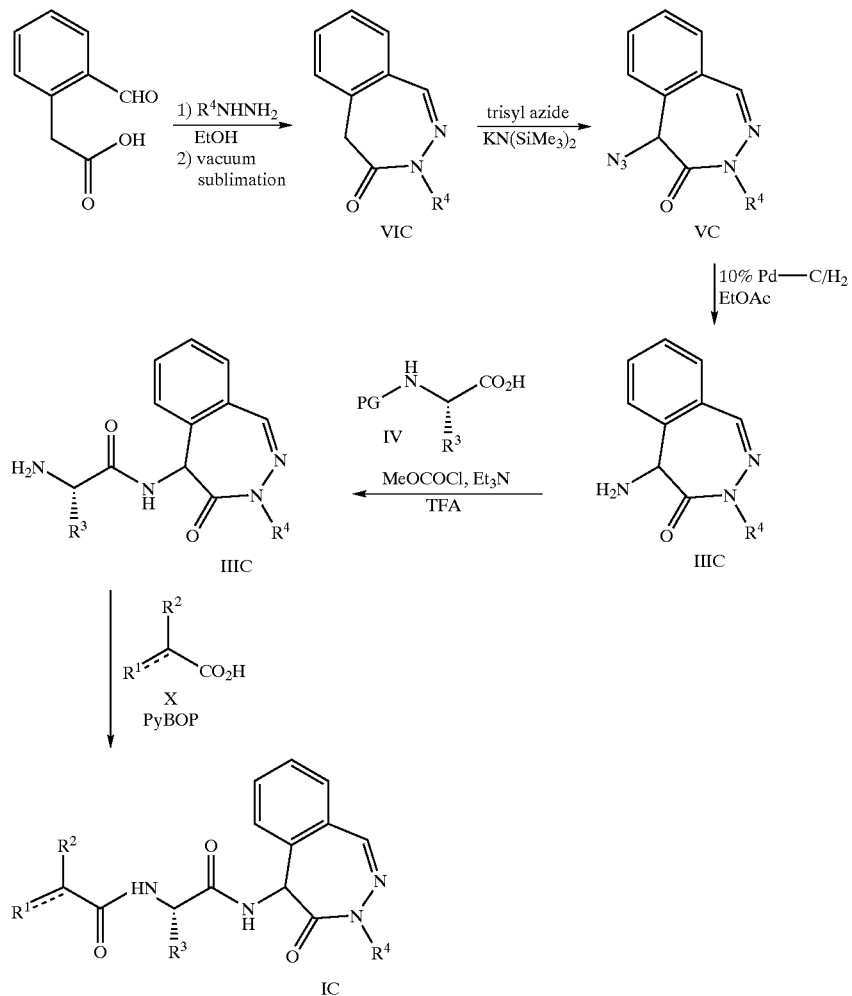

What is claimed is:

1. A compound of Formula I or its stereoisomers,

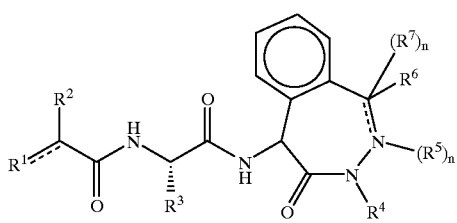

I pharmaceutically acceptable salts or hydrates thereof wherein $R^1$ is hydrogen, hydroxyl, or oxo;

$R^2$ is $C_{1-6}$ alkyl, $C_{2-6}$ alkenyl or alkynyl, $C_{3-7}$ cycloalkyl, $C_{5-7}$ cycloalkenyl, aryl, heteroaryl,

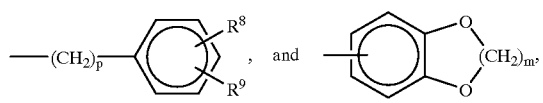

with aryl being phenyl or naphthyl, and heteroaryl being furanyl, thienyl, or pyridinyl;

$R^3$ and $R^4$ are independently selected from $C_{1-6}$ alkyl;

$R^5$ and $R^6$ are independently selected from hydrogen, $C_{1-6}$ alkyl, $C_{2-6}$ alkenyl or alkynyl, $C_{3-7}$ cycloalkyl, $C_{5-7}$ cycloalkenyl,

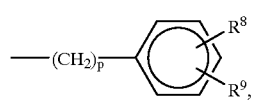

and $-CO_2R^{10}$;

$R^7$ is hydrogen or can be taken with $R^6$ as =O;

$R^8$ and $R^9$ are independently selected from hydrogen, halogen, trifluoromethyl, $C_{1-6}$ alkyl or alkoxy;

$R^{10}$ is $C_{1-6}$ alkyl;

n is zero or one;

m is one or two;

p is zero, one or two; and the solid and dotted lines are either a single or a double covalent bond with the proviso that when they represent a double bond in the benzodiazepinone ring, n is zero.

2. The compound of claim 1 wherein $R^6$ and $R^7$ are taken together as =O.

3. The compound of claim 1 wherein $R^7$ is hydrogen and n is one.

4. The compound of claim 1 wherein n is zero and there is a double bond in the benzodiazepinone ring.

5. The compound of claim 1 wherein $R^2$ is thienyl or

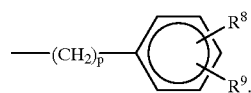

6. The compound of claim 2 wherein $R^2$ is thienyl or

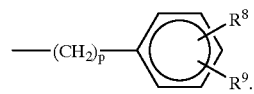

7. The compound of claim 3 wherein $R^2$ is thienyl or

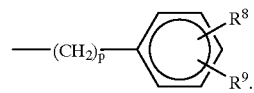

8. The compound of claim 4 wherein $R^2$ is thienyl or

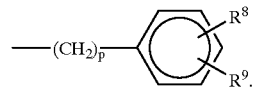

9. A pharmaceutical composition comprising a therapeutically effective amount of a compound of claim 1 in association with a pharmaceutically acceptable carrier or diluent.

* * * * *